(12) United States Patent
Someya et al.

(10) Patent No.: US 9,205,245 B2
(45) Date of Patent: Dec. 8, 2015

(54) MALE-SIDE AND FEMALE-SIDE CONNECTORS FOR CONNECTING FIRST AND SECOND INFUSION TUBES

(75) Inventors: Minoru Someya, Ibaraki (JP); Seiichi Iida, Ibaraki (JP)

(73) Assignee: KABUSHIKI KAISHA TOP, Tokyo (JP)

( * ) Notice: Subject to any disclaimer, the term of this patent is extended or adjusted under 35 U.S.C. 154(b) by 0 days.

(21) Appl. No.: 13/980,261

(22) PCT Filed: Sep. 28, 2011

(86) PCT No.: PCT/JP2011/072260
§ 371 (c)(1),
(2), (4) Date: Jul. 17, 2013

(87) PCT Pub. No.: WO2012/098736
PCT Pub. Date: Jul. 26, 2012

(65) Prior Publication Data
US 2013/0304038 A1    Nov. 14, 2013

(30) Foreign Application Priority Data

Jan. 18, 2011   (JP) .................................. 2011-008060

(51) Int. Cl.
*A61M 25/16*   (2006.01)
*A61M 39/10*   (2006.01)

(52) U.S. Cl.
CPC ..................................... *A61M 39/10* (2013.01)

(58) Field of Classification Search
CPC .............................. A61M 39/10; A61M 39/02
USPC ........................................................... 604/533
See application file for complete search history.

(56) References Cited

U.S. PATENT DOCUMENTS 4,629,455 A  * 12/1986  Kanno ........................... 604/241
5,405,340 A      4/1995  Fageol et al.
2003/0184090 A1 10/2003  Guala

FOREIGN PATENT DOCUMENTS

| DE | 198 33 181 C1 | 1/2000 |
|---|---|---|
| EP | 0 204 311 A2 | 12/1986 |
| JP | 60-129941 U | 8/1985 |
| JP | 60-144443 U | 9/1985 |
| JP | 2005-466 A | 1/2005 |
| JP | 2005-110842 A | 4/2005 |
| JP | 2005-195044 A | 7/2005 |
| WO | WO 84/00595 A1 | 2/1984 |
| WO | WO 2004/035129 A1 | 4/2004 |

* cited by examiner

*Primary Examiner* — Jason Flick
(74) *Attorney, Agent, or Firm* — Birch, Stewart, Kolasch & Birch, LLP (57) ABSTRACT

A female-side connector having a lock mechanism for obtaining a favorable fastening force constantly. The female-side connector includes a central axis of a root in a male screw portion of a female-side lock portion that is screwed together with a female screw portion of a male-side lock portion in a male-side connector that intersects at a predetermined angle relative to a central axis of a thread.

13 Claims, 5 Drawing Sheets

FIG.5

MALE-SIDE AND FEMALE-SIDE CONNECTORS FOR CONNECTING FIRST AND SECOND INFUSION TUBES

TECHNICAL FIELD

The present invention relates to a female-side connector for connecting infusion tubes.

BACKGROUND ART

Conventionally, as a connector for performing connection of a three-way stopcock and infusion tubes such as transfusion tubes, there has been known a tapered type connector having a lock mechanism (for example, refer to Patent Literature 1). A male-side connector constituting the connector is equipped with a lock ring having a female screw, about a male luer. Further, a female-side connector is equipped with a female luer fitted to the male luer, and a male screw screwing with the female screw of the lock ring.

The female-side connector and the male-side connector are coupled by screwing together the male screw and the female screw, while fitting the male luer and the female lure together, and the coupling is being locked thereby. Further, in a vicinity of an end portion of a screw ridge of the male screw, a latch portion by a resilient member is provided, so that, with respect to screwing together of the male screw and the female screw, the screwing together of the male screw and the female screw is fixed by the screw ridge of the female screw of the lock ring running onto the latch portion.

CITATION LIST

Patent Literature

Patent Literature 1: Japanese Patent Application Laid-Open No. 2005-466

SUMMARY OF INVENTION

Technical Problem

However, according to the lock mechanism of the conventional connector explained above, the latch portion is flattened by the thread ridge when the thread ridge runs onto the latch portion, so that there is a fear that favorable fastening force may not be obtained, when the lock mechanism is made to function by connecting the connector again.

An object of the present invention is, in view of such problems of the prior art, to provide a female-side connector constituting a lock mechanism in which favorable fastening force is obtained constantly.

Solution to Problem

In order to achieve the above-mentioned object, a female-side connector according to the present invention is a female-side connector of a connector connecting a first infusion tube and a second infusion tube, wherein: a male-side connector of the connector comprises a male-side coupling flow path which is connected at a base end side thereof to the first infusion tube, and which includes at a leading end side thereof a conical outer surface in which a diameter gradually decreases toward the leading end, and a male-side lock portion which is cylindrical and is held rotatably to an outer periphery of the conical outer surface, and which includes a female screw at an inner periphery surface; the female-side connector comprises a female-side coupling flow path which is connected at a base end side thereof with the second infusion tube, and which includes at a leading-end side with a conical inner surface corresponding to the conical outer surface, and a female-side lock portion which includes a male screw corresponding to the female screw; and a central axis of a thread and a central axis of a root of the male screw intersects at a predetermined angle.

In this configuration, since the central axis of the thread and the central axis of the root of the male screw intersects each other at a predetermined angle, there are portions where a distance from the central axis of the thread to a bottom portion of the root on a plane including the central axis of the thread and the central axis of the root of the male screw is larger than a distance from the central axis of the thread to the bottom portion of the root on a plane which is perpendicular to the plane. and which includes the central axis of the thread. This portion contributes to reliably locking the coupling of the male-side connector and the female-side connector.

That is, when coupling the male-side connector and the female-side connector in order to connect the first infusion tube and the second infusion tube, the conical outer surface of the male-side coupling flow path and the conical inner surface of the female-side coupling flow path are fitted together, and the male screw of the female-side lock portion and the female screw of the male-side lock portion are screwed together. By doing so, the female-side coupling flow path and the male-side coupling flow path are combined, and the bottom portion of the root of the portion of the male screw in which the distance from the central axis of the thread to the bottom portion of the root is larger and an apex portion of the thread of the female screw press against each other, and the male screw and the female screw are fastened. By doing so, the male-side connector and the female-side connector are coupled, and the coupling is locked by the fastening of the male screw and the female screw.

At this time, the fastening force of the male screw and the female screw is generated since the pressing between the apex portion of the thread of the female screw and the bottom portion of the root of the male screw is performed through a pressing surface of an appropriate size, so that a fastening force is not degraded even in the case where the coupling and locking of the male-side connector and the female-side connector are performed repeatedly. Therefore, according to the present invention, the coupling of the female-side connector and the male-side connector may be reliably locked, by a favorable fastening force constantly.

In the present invention, a distance from the central axis of the root to a bottom portion of the root on a plane including the central axis of the thread and the central axis of the root of the male screw is larger than a distance from the central axis of the root to the bottom portion of the root on a plane which is perpendicular to the plane and which includes the central axis of the root.

By doing so, the portion in which the distance from the central axis of the thread in the direction perpendicular to the central axis of the thread to the bottom of the root on the plane including the central axis of the thread and the central axis of the root of the male screw is larger than the distance from the central axis of the thread to the bottom portion of the root on the plane which is perpendicular to the plane and which includes the central axis of the thread increases, so that it becomes possible to lock the coupling of the female-side connector and the male-side connector with a more reliable and more favorable fastening force.

In the present invention, it is preferable that a cross-section perpendicular to the central axis of the root of a tubular surface including the bottom portion of the root has a elliptical shape having a line of intersection between a plane including the central axis of the thread and the central axis of the root of as a long axis. By doing so, it becomes possible to smoothly increase a pressing force, upon pressing of the bottom portion of the root of the male screw and the apex portion of the thread of the female screw, and to smoothly perform fastening of the male screw and the female screw.

In the present invention, in a predetermined range from a leading end of the male screw, the male screw may have a normal shape of the male screw in which the central axis of the thread and the central axis of the root of the male screw coincide. By doing so, upon coupling and locking the female-side connector and the male-side connector, it becomes possible to perform fitting of the female screw and the male screw smoothly.

In the present invention, the female-side connector may include a base portion having a supporting surface which supports the base end of the female-side lock portion, and the thread of the male screw may be coupled to the supporting surface at a portion of a base end portion of the male screw, which is a portion intersecting with a plane including the central axis of the root and the central axis of the thread, and a portion where the supporting surface and the central axis of the root makes an acute angle.

By doing so, although stress tends to concentrate on the base end of the male screw of the female-side lock portion on the side making the acute angle, it becomes possible to increase a strength with respect to the applied stress, since the base end is combined to the supporting surface as the thread of the male screw.

In the present invention, the female screw and the male screw may be double-threaded screw. By doing so, it becomes possible to make the pressing between the apex portion of the thread of the female screw and the bottom portion of the root of the male screw generate at approximately symmetrical portions with respect to the central axis of the connector. By doing so, it becomes possible to perform coupling of the male-side connector and the female-side connector smoothly.

In this case, the central axis of the root intersecting with the central axis of the thread of the male screw may be the central axis of the root of one of the two roots of the male screw, and the central axis of the other root may coincide with the central axis of the thread of the male screw.

By doing so, it becomes possible to configure the male screw, so that the portion in which the distance to the bottom portion of the root is larger exists at two places in the vicinity of a starting portion and a terminating portion of the one of the root. By doing so, it becomes possible to reliably fasten the male screw and the female screw, and to more reliably lock the coupling of the male-side connector and the female-side connector.

BRIEF DESCRIPTION OF DRAWINGS

FIG. 1A is a plane view, FIG. 1B is a front view.

DESCRIPTION OF EMBODIMENTS

Figure 1A:
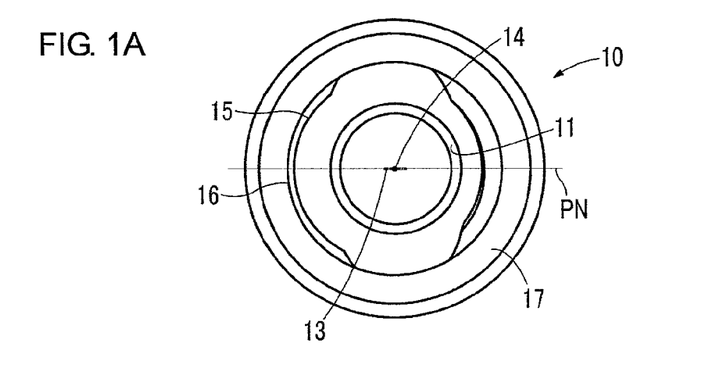
Figure 1B:
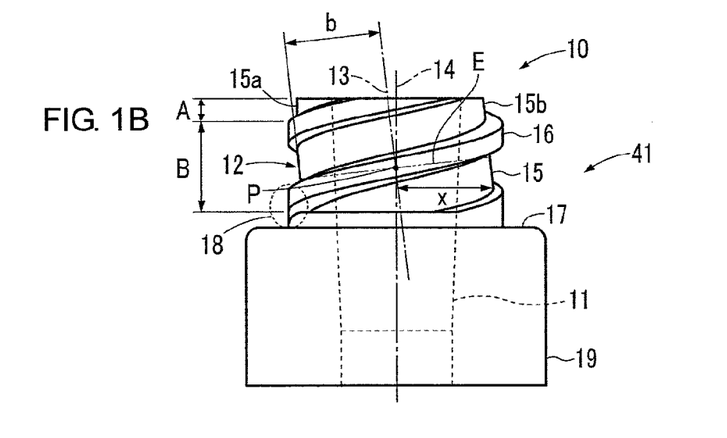
Figure 1C:
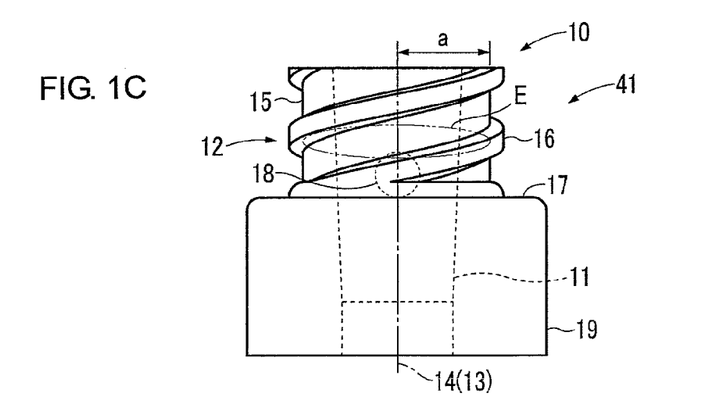
FIG. 1C is a side view of a tapered-style female-side connector according to an embodiment of the present invention.
Figure 2:
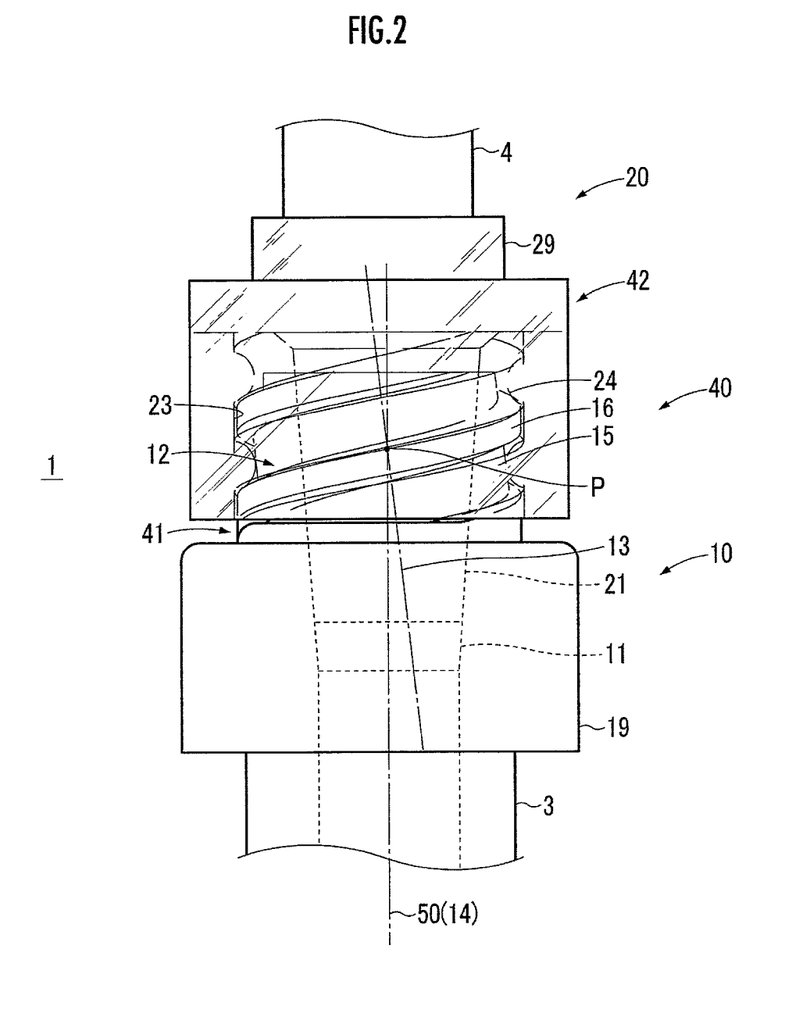
FIG. 2 is a front view showing a state in which a tapered-style male-side connector is coupled to the female-side connector shown in FIG. 1.

Hereinafter, embodiments of the present invention will be explained with reference to the drawings. FIG. 1 is a trihedral figure of a female-side connector constituting a tapered-style connector according to one embodiment of the present invention. In the figure, 1A is a plane view, 1B is a front view, and 1C is a side view. FIG. 2 is a front view showing a state in which a male-side connector is coupled to the female-side connector of FIG. 1.

As is shown in these figures, a connector 1 connecting an infusion tube 3 and an infusion tube 4 is equipped with a female-side connector 10 provided at an end portion of the infusion tube 3, and a male-side connector 20 provided at an end portion of the infusion tube 4. A part of the female-side connector 10 and a part of the male-side connector 20 constitute a lock mechanism 40 which fixes a connection of the connector 1.

The female-side connector 10 is equipped with a cylindrical base portion 19 which is fixed to the end portion of the infusion tube 3, a cylindrical female-side lock portion 41 which is supported by the base portion 19 and which constitutes the lock mechanism 40, and a female-side coupling flow path 11, a base-end side of which is connected to the infusion tube 3, and a leading-end side of which is opened at a leading end surface of the female-side lock portion 41. An inner surface of the leading-end side of the female-side coupling flow path 11 is a tapered surface (conical inner surface) in which a diameter gradually increases towards the leading end.

The female-side lock portion 41 is equipped with a male screw portion 12 constituted from a trapezoidal thread provided to its outer wall. The male screw portion 12 is equipped with a root 15 and a thread 16 constituting the trapezoidal thread. As is shown in FIGS. 1B and 1C, in a second range B which is a remainder of excluding a predetermined first range A from a leading end of the male screw portion 12, a central axis 13 of the root 15 intersects a central axis 14 of the thread 16 at an intersection P, at a predetermined angle, for example 6.5°. The intersection P is positioned at an approximately center of the second range B.

The male screw portion 12 has a normal male screw shape in which the central axis 14 of the thread 16 and the central axis 13 of the root 15 of the male screw portion 12 coincide, in the above-mentioned first range A, for example in a range of ½ to 1 pitch of the screw thread. Further, in the first range A, the central axis of the female-side coupling flow path 11 coincides with the central axis 14.

Further, in the above-mentioned second range B, there are portions where a distance x (FIG. 1B) from the central axis 14 to a bottom portion of the root 15 on a plane PN (FIG. 1A) including the central axis 14 and the central axis 13 is larger than a distance a (FIG. 1C) from the central axis 14 to the bottom portion of the root 15 in a plane which is perpendicular to the plane PN and which includes the central axis 14. The distance a corresponds to a distance between a central axis of a male screw portion in a conventional female-side lock portion, in which central axes of the thread and the bottom coincides, to a bottom portion of the root thereof.

Figure 5:
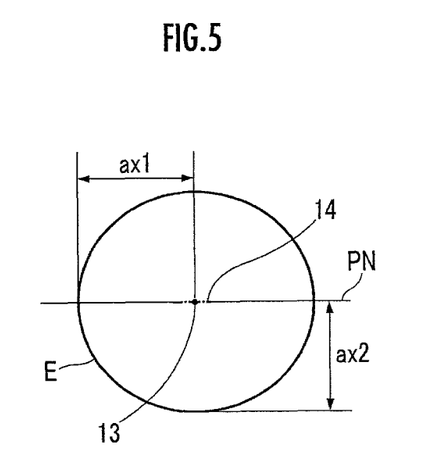
FIG. 5 is a view showing a cross-sectional shape of a tubular surface including a bottom portion of a root of a male screw portion in the female-side connector shown in FIG. 1.

Further, in the above-mentioned second range B, in a case where a cylindrical surface including the bottom portion of the root 15 is being considered, a cross-section perpendicular to the central axis 13 of the cylindrical surface has, as is shown in FIG. 5, an elliptical shape taking a line of intersection with the plane PN including the central axis 14 and the central axis 13 as a long axis. A long radius ax1 of an ellipse E is equal to a distance b (FIG. 1B) from the central axis 13 to the bottom portion of root 15 on the plane PN. Further, a short radius ax2 is approximately equal to the above-mentioned distance a. The lengths of the long axis and a short axis of the ellipse E are, for example, 6.9 mm and 6.5 mm, respectively.

That is, in the second range B, the distance b (=ax1) from the central axis 13 to the bottom portion of the root 15 on the plane PN including the central axis 14 of the thread 16 and the central axis 13 of the root 15 is larger than a distance (=ax2) from the central axis 13 to the bottom portion of the root 15 on a plane which is perpendicular to the plane PN and which includes the central axis 13.

In FIG. 1B which is a front view, a state where the female-side connector is viewed from a direction perpendicular to the plane PN (FIG. 1A) including the central axis 13 and the central axis 14 is shown. In FIG. 1C which is a side view, a state where the female-side connector is viewed from a direction parallel to the plane PN is shown. Therefore, in FIG. 1C, the central axis 13 and the central axis 14 appears to coincide with each other.

As is shown in FIG. 1B, lateral end portions of an upper end of the male screw portion 12 in the first range A are the roots 15a and 15b. Distances from the central axis 14 to bottom portions of the roots 15a and 15b are similar distance to the distance a from the central axis 14 to the bottom portion of the root 15 in the side view of FIG. 1C.

In the female-side connector 10, among the base-end portion of the male screw portion 12 in the second range B, a portion 18 which intersects a surface including the central axes 13 and 14, and which is on a side where a supporting surface 17 of the base portion 19 supporting the female-side lock portion 41 and the central axis 13 of the root 15 makes an acute angle, the thread 16 is combined to the supporting surface 17. By doing so, an intensity with respect to a stress applied to the portion 18 is increased.

As is shown in FIG. 2, the male-side connector 20 is equipped with a cylindrical base portion 29 fixed to the end portion of the infusion tube 4, a cylindrical male-side lock portion 42 which is supported by the base portion 29, and which constitutes the lock mechanism 40, and a male-side coupling flow path 21 of a tapered tube, a base-end side of which is connected to an end portion of the infusion tube 4, and a leading-end side of which protrudes slightly from a leading-side end portion of the male-side lock portion 42. An outer surface of the tapered tube is a tapered surface (a conical outer surface) in which a diameter decreases towards the leading end.

The male-side lock portion 42 is configured from a cylindrical transparent member, with a base-end side being supported by the base portion 29, and a leading-end side being opened. The supporting of the male-side lock portion 42 by the base portion 29 is performed so that the male-side lock portion 42 becomes freely rotatable at an outer periphery of the tapered surface (the conical outer surface) of the male-side coupling flow path 21. To an inner side of the male-side lock portion 42, a female screw portion 23 which screws together with the male screw portion 12 of the female-side lock portion 41 is provided. The female screw portion 23 and the male screw portion 12 are configured by a double-threaded screw.

The female-side connector 10 and the male-side connector 20 are configured such that, when the male screw portion 12 and the female screw portion 23 are screwed together with the tapered surfaces of the female-side coupling flow path 11 and the male-side coupling flow path 21 are mutually fitted together, the female-side coupling flow path 11 and the male-side coupling flow path 21 are coupled, and also a thread 24 of the female screw portion 23 and the root 15 of the above-mentioned portion in which the distance x from the central axis 14 is larger slide and then press against each other, so that the coupling is locked by this pressing force.

In such configuration, when connecting the infusion tube 3 and the infusion tube 4, the female-side connector 10 and the male-side connector 20 are pressed against each other while facing the tapered surface of the male-side coupling flow path 21 with respect to the tapered surface of the female-side coupling flow path 11, and are rotated in a direction in which a right screw relatively advances about an axis 50 of the connector 1, so as to screw the male screw portion 12 and the female screw portion 23 together.

At this time, when the male screw portion 12 and the female screw portion 23 are being screwed together, the thread 24 of the female screw portion 23 reaches the portion of the root 15 in which the distance x from the central axis 14 to the bottom portion of the root 15 of the male screw portion 12 is larger than a predetermined value. Then, the thread 24 of the female screw portion 23 and the root 15 of the male screw portion 12 slide and then press against each other via a comparatively large contact surface, and are combined. As a result, the female-side coupling flow path 11 and the male-side coupling flow path 21 are coupled together, and also the female-side lock portion 41 and the male-side lock portion 42 are coupled together and fixed. This completes the connection between the infusion tube 3 and the infusion tube 4.

Figure 3A:
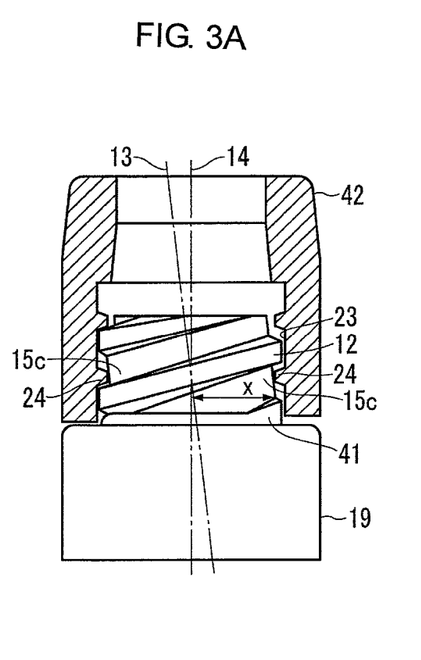
FIG. 3A is an explanatory view for explaining a principal of coupling of a female-side lock portion and a male-side lock portion in the female-side connector shown in FIG. 1.
Figure 3B:
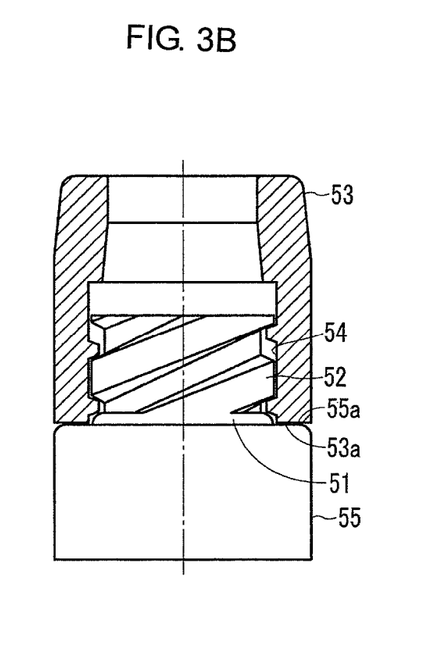
FIG. 3B is an explanatory view for explaining the principal in a conventional female-side connector.

FIG. 3 is a view showing a principle of the coupling of the female-side lock portion 41 and the male-side lock portion 42, by comparing with the case of a conventional female-side lock portion and a male-side lock portion. FIG. 3A shows a case of the present embodiment, and FIG. 3B shows a conventional case.

In the conventional case, as is shown in FIG. 3B, when a male screw portion 52 of a female-side lock portion 51 and a female screw portion 54 of a male-side lock portion 53 are screwed together, a fastening force is generated by an end surface 55a of a base portion 55 supporting the male screw portion 52 contacting an end surface 53a of the male-side lock portion 53. Therefore, the fastening force is weak, and there are cases where the male screw portion 52 or the female screw portion 54 rotates easily after fastening, and the lock is released.

In contrast thereto, in the case of the present embodiment, as is shown in FIG. 3A, when the male screw portion 12 of the female-side lock portion 41 and the female screw portion 23 of the male-side lock portion 42 are screwed together, the thread 24 of the female screw portion 23 and the bottom portion of a root 15c of the portion in which the above-mentioned distance x from the central axis 14 is larger slide and press against each other, so as to fix the female-side lock portion 41 and the male-side lock portion 42 with a favorable fastening force.

In doing so, the fastening force is generated by the pressing of the thread 24 and the root 15c, via a pressing surface of an appropriate area, so that the fastening force is not degraded even in the case where the locking by the female-side lock portion 41 and the male-side lock portion 42 are performed repeatedly.

As is explained above, according to the present embodiment, when the male screw portion 12 and the female screw portion 23 are screwed together, the locking of the male-side lock portion 42 and the female-side lock portion 41 is performed by the thread 24 of the female screw portion 23 and the bottom portion of the root 15c of the portion in which the distance x from the central axis 14 of the male screw portion 12 is larger press against each other, so that the locking may be performed constantly with a favorable fastening force.

Figure 4A:
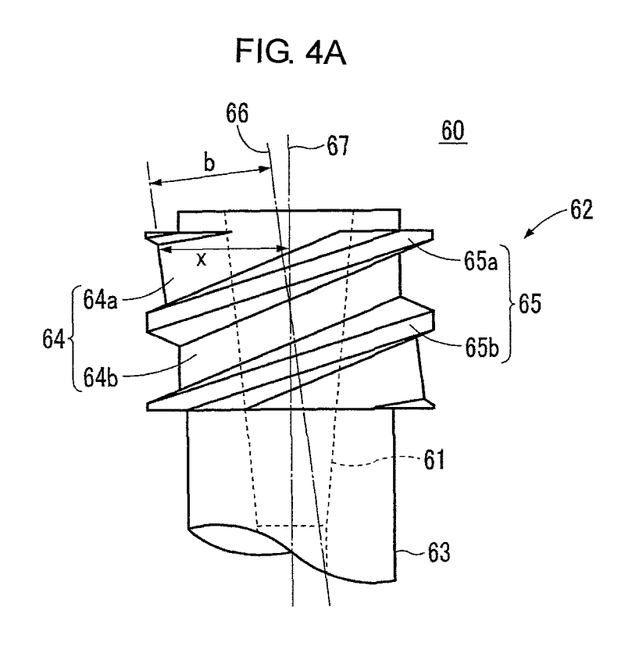
FIG. 4A is a front view and FIG. 4B is a side view of the tapered-style female-side connector according to another embodiment of the present invention.
Figure 4B:
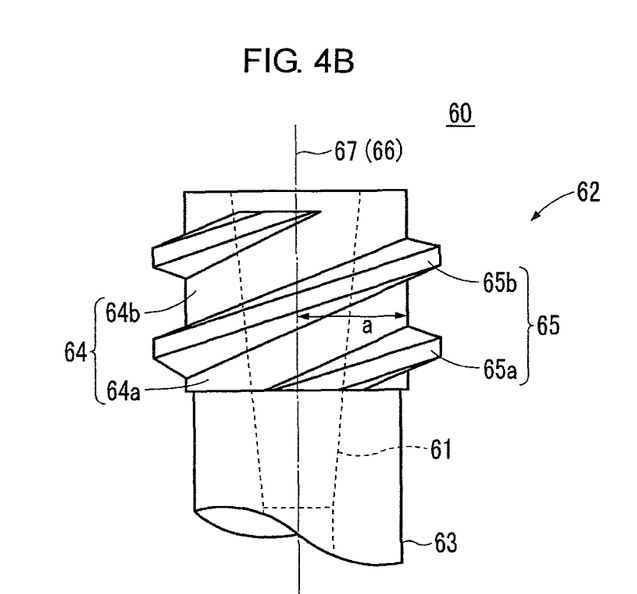

FIG. 4 shows a female-side connector according to another embodiment of the present invention. FIG. 4A is a front view, and FIG. 4B is a side view. As is shown in FIG. 4, a female-side connector 60 is equipped with a female-side coupling flow path 61 to which the male-side coupling flow path 21 of the male-side connector 20 shown in FIG. 2 is coupled, and a male screw portion 62 to which the female screw portion 23 of the male-side lock portion 42 provided in the male-side connector 20 is screwed. The male screw portion 62 constitutes the female-side lock portion.

To an inner surface of a leading-end side of the female-side coupling flow path 61, a tapered surface corresponding to the tapered surface of the male-side coupling flow path 21 is provided. The female-side connector 60 is provided to an end portion of an infusion tube 63, and is used for connecting the infusion tube 63.

The male screw portion 62 is configured from a double-threaded screw of a trapezoidal thread. Therefore, the male screw portion 62 has two roots 64a and 64b as a root 64, and has two threads 65a and 65b as a thread 65. Central axes of the threads 65a and 65b coincide, and this central axis is a central axis 67 of the thread 65. A central axis 66 of the root 64a intersects with the central axis 67 of the thread 65 at a predetermined angle. A central axis of the root 64b coincides with the central axis 67 of the thread 65.

In the case where the female-side connector is viewed from the side surface side, such as in FIG. 4B, the central axis 66 of the root 64a and the central axis 67 of the thread 65 coincide. Further, on a plane including the central axis 67 and which is perpendicular to the plane including the central axis 66 and the central axis 67, distances from the central axis 67 to each of the bottom portions of the roots 64a and 64b are approximately identical. This distance is denoted as a distance a.

A distance x (FIG. 4A) on the plane including the central axis 66 and the central axis 67 from the central axis 67 to the bottom portion of the root 64a is larger than the above-mentioned distance a.

Further, in the case where a tubular surface including the bottom portion of the root 64a is being considered, a cross-section in the direction perpendicular to the central axis 66 of the tubular surface has an elliptical shape taking a line of intersection with the plane including the central axis 66 and the central axis 67 as a long axis. That is, a long radius of the elliptical shape is a distance b (FIG. 4A) from the central axis 66 to the bottom portion of the root 64a on the surface including the central axis 66 and the central axis 67.

As is shown in FIG. 4A, in the case where the female-side connector is viewed from the front surface side, the distance to the bottom portion of the root 64b from the central axis 67 is a distance similar to the distance a from the central axis 67 to the bottom portion of the root 64b, in the case where the same is viewed from the side surface side in FIG. 4B. That is, the male screw portion 62 has, with respect to the root 64b, a shape of a regular male screw in which the central axis 67 of the thread 65 and the central axis of the root 64b coincide. The central axis of the female-side coupling flow path 61 coincides with the central axis 67.

In this configuration, connecting of the infusion tube 63 and the infusion tube 4 (FIG. 2), and the locking of the connection may be performed similarly to those in the case of the above-mentioned female-side connector 10. Also, from the reasons similar to hose of the case of the female-side connector 10, coupling of the female-side connector 60 and the male-side connector 20 may be reliably locked, from constantly favorable fastening force.

The portion in which the distance x from the central axis 67 to the bottom portion of the root 64a is larger exists, as is shown in FIG. 4, in two places in the vicinity of a starting portion and a terminating portion of the root 64a, so that these two portions contribute to generation of the favorable fastening force.

The present invention is not limited to the above-mentioned embodiments, and may be arbitrarily modified and implemented. For example, in the above-mentioned embodiments, those configured from the double-threaded screw are used as the female screw portion 23 and the male screw portion 12. However, it is not limited thereto, and those configured from other shapes, for example from a single-threaded screw may be used.

Further, in the above-mentioned embodiments, no reference was made with respect to material of each portion. However, the fastening force between the female screw portion 23 and the male screw portion 12 or 62 is generated by performing pressing between the thread 24 of the above-mentioned female screw portion 23 and the root 15c or 64a of the male screw portion 12 or 62, so that the favorable fastening force may be generated easily even when the female screw portion 23 and the male screw portion 12 or 62 are made of a comparatively rigid material.

Therefore, the female screw portion 23 and the male screw portion 12 or 62 may be configured from a comparatively rigid material, for example from a polycarbonate. In this case, even in the case where the locking of the male-side connector 20 and the female-side connector 10 or 60 is repeated, the fastening force does not deteriorate. Therefore, coupling of the female-side connector 10 or 60 and the male-side connector 20 may be locked constantly with the favorable fastening force.

In the case where the male screw portion 12 or 62 is configured from a comparatively soft polypropylene, and the female screw portion 23 is configured from a comparatively rigid polycarbonate, the deterioration of the fastening force is slightly accelerated.

INDUSTRIAL APPLICABILITY

The female-side connector provided to the infusion tube is used for reliably connecting two infusion tubes, by connecting the male-side connector of another infusion pipe thereto, and by operating the lock mechanism. At this time, the female-side connector may be used as the one suitable for connecting the infusion tubes of a medical solution and the like, while maintaining the function of the lock mechanism favorably without deteriorating the same.

REFERENCE SIGNS LIST

1 . . . connector, 3, 4, 63 . . . infusion tube, 10, 60 . . . female-side connector, 11, 61 . . . female-side coupling flow path, 12, 62 . . . male screw portion, 13, 14, 66, 67 . . . central axis, 15, 15a, 15b, 15c, 64, 64a, 64b . . . root, 16, 24, 65, 65a, 65b . . . thread, 19 . . . base portion, 20 . . . male side connector, 21 . . . male side coupling flow path, 23 . . . female screw portion, 41 ... female-side lock portion, 42 ... male-side lock portion, E ... ellipse, PN ... plane

The invention claimed is:

1. A connector comprising a male-side connector and a female-side connector connecting a first infusion tube and a second infusion tube, wherein:
   the male-side connector comprises a male-side coupling flow path which is connected at a base end side thereof to the first infusion tube, and which includes at a leading end side thereof a conical outer surface in which a diameter gradually decreases toward the leading end, and a male-side lock portion which is cylindrical and is held rotatably to an outer periphery of the conical outer surface, and which includes a female screw at an inner periphery surface;
   the female-side connector comprises a female-side coupling flow path which is connected at a base end side thereof with the second infusion tube, and which includes at a leading-end side with a conical inner surface corresponding to the conical outer surface, and a female-side lock portion which includes a male screw corresponding to the female screw;
   the male screw comprising a tubular portion and a spiral portion which spirally extends on an outer peripheral surface of the tubular portion;
   the outer peripheral surface of the tubular portion configures a bottom portion of a root of the male screw;
   the spiral portion configures a thread of the male screw;
   a central axis of the tubular portion comprises a central axis of the root;
   a central axis of the spiral portion comprises a central axis of the thread; and
   the central axis of the thread and the central axis of the root intersect at a predetermined angle;
   wherein a cross-section perpendicular to the central axis of the root of the outer peripheral surface of the tubular portion has an elliptical shape, and a long axis of the elliptical shape is located on a plane including the central axis of the thread and the central axis of the root.

2. A connector comprising a male-side connector and a female-side connector connecting a first infusion tube and a second infusion tube, comprising:
   a male-side coupling flow path formed in said male-side connector, said male-side coupling flow path is connected at a base end side thereof to the first infusion tube, and includes at a leading end side thereof a conical outer surface having a diameter gradually decreasing toward the leading end, and a male-side lock portion which is cylindrical and is held rotatably to an outer periphery of the conical outer surface, and which includes a female screw at an inner periphery surface;
   a female-side coupling flow path formed in said female-side connector, said female-side coupling flow path is connected at a base end side thereof with the second infusion tube, and includes at a leading-end side with a conical inner surface corresponding to the conical outer surface, and a female-side lock portion which includes a male screw corresponding to the female screw;
   the male screw comprising a tubular portion and a spiral portion which spirally extends on an outer peripheral surface of the tubular portion;
   the outer peripheral surface of the tubular portion configures a bottom portion of a root of the male screw;
   the spiral portion configures a thread of the male screw;
   a central axis of the tubular portion extends longitudinally relative to the connector and comprises a central axis of the root;
   a central axis of the spiral portion extends longitudinally relative to the connector and comprises a central axis of the thread; and
   the central axis of the thread extending longitudinally relative to the connector and the central axis of the root extending longitudinally relative to the connector intersect at a predetermined angle that is greater than 0°.

3. The connector according to claim 2, wherein a distance from the central axis of the root to the bottom portion of the root on a first plane including the central axis of the thread and the central axis of the root is larger than a distance from the central axis of the root to the bottom portion of the root on a second plane which is perpendicular to the first plane and which includes the central axis of the root.

4. The connector according to claim 2, wherein, in a predetermined range from a leading end of the male screw, the male screw has a shape in which the central axis of the thread and the central axis of the root coincide.

5. The connector according to claim 2,
   wherein the female-side connector includes a base portion having a supporting surface supporting the base end of the female-side lock portion, and
   the thread of the male screw is coupled to the supporting surface at a portion of a base end portion of the male screw, which is the portion of the base end portion intersecting with a plane including the central axis of the root and the central axis of the thread, and the portion of the base end portion of a side where the supporting surface and the central axis of the root makes an acute angle.

6. The connector according to claim 2, wherein the female screw and the male screw are double-threaded screws.

7. The connector according to claim 6, wherein the central axis of the root intersecting with the central axis of the thread is a central axis of one of the root of two roots of the male screw, and a central axis of another root coincides with the central axis of the thread of the male screw.

8. A connector element having a male screw, wherein:
   the male screw comprises a tubular portion and a spiral portion which spirally extends on an outer peripheral surface of the tubular portion;
   the outer peripheral surface of the tubular portion configures a bottom portion of a root of the male screw;
   the spiral portion configures a thread of the male screw;
   a central axis of the tubular portion and a central axis of the spiral portion intersect at a predetermined angle which is more than 0°.

9. The connector according to claim 8, wherein a distance from the central axis of the root to the bottom portion of the root on a first plane including the central axis of the thread and the central axis of the root is larger than a distance from the central axis of the root to the bottom portion of the root on a second plane which is perpendicular to the first plane and which includes the central axis of the root.

10. The connector according to claim 8, wherein a cross-section perpendicular to the central axis of the root of the outer peripheral surface of the tubular portion has an elliptical shape, and a long axis of the elliptical shape is located on a plane including the central axis of the thread and the central axis of the root.

11. The connector according to claim 8, wherein, in a predetermined range from a leading end of the male screw, the male screw has a shape in which the central axis of the thread and the central axis of the root coincide.

12. The connector according to claim 8, wherein the female screw and the male screw are double-threaded screws.

13. The connector according to claim 12, wherein the central axis of the root intersecting with the central axis of the thread is a central axis of one of the root of two roots of the male screw, and a central axis of another root coincides with the central axis of the thread of the male screw.

* * * * *